United States Patent
Dilnik et al.

(12) 
(10) Patent No.: US 6,627,289 B1
(45) Date of Patent: *Sep. 30, 2003

(54) MECHANICAL FASTENING TAPES AND METHOD FOR THEIR CONSTRUCTION

(75) Inventors: Rebecca Lyn Dilnik, Appleton, WI (US); Allen Todd Leak, Neenah, WI (US); Mark Michael Mleziva, Appleton, WI (US); Michael A. Snyder, Waupaca, WI (US); Patrick Sean McNichols, Hortonville, WI (US); Scott Leslie Williams, Neenah, WI (US); Robert John Leveille, Appleton, WI (US); Scott Lee Pennings, Neenah, WI (US); Paul John Serbiak, Appleton, WI (US); Bruce Michael Siebers, Appleton, WI (US); Robert Eugene Vogt, Neenah, WI (US); Georgia Lynn Zehner, Larsen, WI (US); Thomas David Ehlert, Neenah, WI (US); John Gerard Hein, Appleton, WI (US); Timothy Raymond Heindel, Neenah, WI (US); Tim Joseph Janssen, Kaukauna, WI (US); Kathleen Ann Peterson, Madison, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/514,223

(22) Filed: Feb. 28, 2000

Related U.S. Application Data

(63) Continuation of application No. 08/442,065, filed on May 16, 1995, now Pat. No. 6,406,467, which is a continuation of application No. 08/263,281, filed on Jun. 21, 1994, now abandoned, which is a continuation of application No. 08/148,130, filed on Nov. 5, 1993, now abandoned, which is a continuation-in-part of application No. 08/105,701, filed on Aug. 17, 1993, now abandoned, said application No. 08/148,130, is a continuation-in-part of application No. 07/906,016, filed on Jan. 26, 1992, now Pat. No. 5,318,555, which is a continuation-in-part of application No. 07/628,251, filed on Dec. 17, 1990, now abandoned, said application No. 08/148,130, is a continuation-in-part of application No. 07/954,094, filed on Sep. 30, 1992, now Pat. No. 5,403,302, which is a division of application No. 07/627,874, filed on Dec. 13, 1990, now Pat. No. 5,176,671, which is a continuation-in-part of application No. 07/287,746, filed on Dec. 20, 1988, now abandoned.

(51) Int. Cl.[7] ............................................. D04H 11/00
(52) U.S. Cl. ........................ 428/92; 604/391; 604/387
(58) Field of Search ................................. 604/391, 387; 428/85, 92

(56) References Cited

U.S. PATENT DOCUMENTS 3,141,461 A   7/1964   Farris .......................... 128/284

(List continued on next page.)

FOREIGN PATENT DOCUMENTS

AU            595002        3/1990

(List continued on next page.)

OTHER PUBLICATIONS

Application of Adhesive Bonding and Welding in the Clothing Industry, Ferenczi M. Magyar Textiltech 30: 647–649 (Dec., 1977) (Abstract only).

(List continued on next page.)

Primary Examiner—Elizabeth M. Cole
(74) Attorney, Agent, or Firm—Brinks Hofer Gilson & Lione

(57) ABSTRACT

Disclosed is an improved fastening tape for use on a disposable absorbent garment. The fastening tape comprises a first substrate and an interlocking material attached to said first substrate. The interlocking material extends the entire width of the fastening tape, and the interlocking material is longitudinally spaced from both transverse edges of the fastening tape. Also disclosed is a process for manufacturing the fastening tape. The process involves providing a continuous length of an interlocking material having a width and traveling in a first direction. The interlocking material is attached to a first substrate to form a composite. The composite is then cut along a second direction to form fastening tapes suitable for attachment on a disposable absorbent garment. The second direction is substantially perpendicular to the first direction.

11 Claims, 11 Drawing Sheets

U.S. PATENT DOCUMENTS

| | | | |
|---|---|---|---|
| 3,359,980 A | 12/1967 | Rosenblatt | 128/284 |
| 4,051,854 A | 10/1977 | Aaron | 128/284 |
| 4,205,679 A | 6/1980 | Repke et al. | 128/287 |
| 4,372,793 A | 2/1983 | Herz | 156/66 |
| 4,486,485 A | 12/1984 | Sookne | 428/198 |
| 4,528,224 A | 7/1985 | Ausnit | 428/36 |
| 4,617,002 A | 10/1986 | Pigneul et al. | 604/391 |
| 4,633,565 A | 1/1987 | DeWoskin | 29/417 |
| 4,655,760 A | 4/1987 | Morman et al. | 604/385 A |
| 4,664,663 A | 5/1987 | Brier | 604/387 |
| 4,798,603 A | 1/1989 | Meyer et al. | 604/378 |
| 4,846,815 A | 7/1989 | Scripps | 604/391 |
| 4,847,134 A | 7/1989 | Fahrenkrug et al. | 428/138 |
| 4,869,724 A | 9/1989 | Scripps | 604/389 |
| 4,894,060 A | 1/1990 | Nestegard | 604/391 |
| 4,946,527 A | 8/1990 | Battrell | 156/60 |
| 4,957,571 A | 9/1990 | Cipolla | 156/66 |
| 4,994,054 A | 2/1991 | Pigneul et al. | 604/391 |
| 5,005,525 A | 4/1991 | Stanton | 119/95 |
| 5,019,065 A | 5/1991 | Scripps | 604/385.1 |
| 5,019,073 A | 5/1991 | Roessler et al. | 604/391 |
| 5,053,028 A | 10/1991 | Zoia et al. | 604/385.1 |
| 5,096,532 A | 3/1992 | Neuwirth et al. | 156/580.1 |
| 5,110,403 A | 5/1992 | Ehlert | 156/580.1 |
| 5,176,668 A | 1/1993 | Bernardin | 604/368 |
| 5,176,671 A | 1/1993 | Roessler et al. | 604/391 |
| 5,176,672 A | 1/1993 | Bruemmer et al. | 604/385.1 |
| 5,192,606 A | 3/1993 | Proxmire et al. | 428/284 |
| 5,266,401 A | 11/1993 | Tollini | 428/343 |
| 5,312,387 A | 5/1994 | Rossini et al. | 604/389 |
| 5,318,555 A | 6/1994 | Siebers | 604/390 |
| 5,399,219 A | 3/1995 | Roessler et al. | 156/259 |
| 5,403,302 A | 4/1995 | Roessler . | 604/391 |
| 5,509,915 A | 4/1996 | Hanson | 604/378 |
| 5,527,302 A | 6/1996 | Endres | 604/385.1 |
| 5,656,111 A | 8/1997 | Dilnik et al. | 156/66 |
| 5,660,666 A | 8/1997 | Dilnik et al. | 156/259 |
| 6,406,467 B1 | 6/2002 | Dilnik et al. | 604/391 |
| 6,406,468 B1 | 6/2002 | Dilnik et al. | 604/391 |

FOREIGN PATENT DOCUMENTS

| | | |
|---|---|---|
| CA | 2056812 | 3/1993 |
| CN | 77200114 | 3/1989 |
| DE | 8704470 | 7/1987 |
| EP | 0103244 | 3/1984 |
| EP | 0233704 | 8/1987 |
| EP | 0 289 198 | 11/1988 |
| EP | 0 321 232 | 6/1989 |
| EP | 0 321 234 | 6/1989 |
| EP | 0388681 | 9/1990 |
| EP | 0433951 | 6/1991 |
| EP | 0235014 | 7/1991 |
| EP | 0491347 | 6/1992 |
| EP | 0539703 | 5/1993 |
| EP | 0563457 | 10/1993 |
| EP | 0563458 | 10/1993 |
| EP | 0 714 273 | 6/1996 |
| GB | 2185383 | 7/1987 |
| GB | 2212382 | 7/1989 |
| GB | 2214057 | 8/1989 |
| JP | 56-161101 | 12/1981 |
| JP | 57-191303 | 11/1982 |
| WO | 92/10957 | 7/1992 |
| WO | 94/13168 | 6/1994 |

OTHER PUBLICATIONS

The Influence of Vibration on the Physical–Mechanical Properties of Nonwovens, Which Were Prepared With Physical–Chemical Technology, by M.M. Stepanov, Ye. N. Bershev, R. Krchma (S.M. Kirov Leningrad Institute for the Textile and Light Industries), Promyshlennosti No. 1 (163): 44–45 (Jan., 1985) (Abstract only).

"New Research Sparks Interest in Threadless Joining", *Daily News Record*, 11, No. 181: 16 (Sep. 21, 1981) (Abstract only).

"The Vario S Adhesive Binding System", *Anon., Fr. Graphique*, No. 11, Nov., 1986, pp. 77–78 (Abstract only).

Notice of Opposition to European Patent 0,714,273, with Statement of Facts and Submissions, filed Feb. 5, 2001, by SCA Hygiene Products AB.

Letter from D. David of Kayersberg SA to Ulf Ekwall of SCA Molnlycke AB, dated Oct. 18, 1996, re "Opposition Against P & G Patent EP 321 234" and enclosures, Opposition Document E2.

Letter from Richard Willoughby of Simmons and Simmons to Daniel David of Kayersberg SA, dated Dec. 05, 1996, re "Lotus Baby Ultra Diaper with Mechanical Fasteners", Opposition Document E3.

Letter from D. David of Kayersberg SA to Richard Willoughby of Simmons and Simmons, dated Dec. 13, 1996, re "Lotus Baby Ultra Diaper with Mechanical Fasteners", Opposition Document E4.

Letter from C. R. Davies of the Office of Frank B. Dehn & Co. to European Patent Office, dated Nov. 8, 1996, re "European Patent 321 234—The Procter & Gamble Company—Opposed by (1) Kimberly–Clark Corporation and (2) Molnycke AB" and enclosures, Opposition Document E5.

Communication of a Notice of Opposition for EP 0,714,273, from European Patent Office to Diehl, Glaeser, Hiltl & Partner, dated 26.02.01 (Feb. 26, 2001).

Further Communication of a Notice of Opposition for EP 0,714,273, from European Patent Office to Diehl, Glaeser, Hiltl & Partner, dated 09.03.01 (Mar. 9, 2001).

Letter from Diehl, Glaeser, Hiltl & Partner to European Patent Office, dated Mar. 26, 2001, re "European Patent 0,714,273 . . . Opposition by SCA Hygiene Products AB . . . ".

Letter from Diehl, Glaeser, Hiltl & Partner to European Patent Office, dated Sep. 18, 2001, re European Patent 0,714,273—"In response to the Communication pursuant to Rule 57(1) EPC dated Mar. 9, 2001".

Letter from Susan Joyce Allard of Boult Wade & Tennant to European Patent Office, dated Feb. 18, 2002, re "Opposition to European Patent 0,714,273B . . . on behalf of SCA Hygiene Products AB . . . "; together with letter from European Patent Office forwarding the same to Diehl, Glaeser, Hiltl & Partner, dated 04.03.02 (Mar. 4, 2002).

"Summons to Attend Oral Proceedings . . . " re European Patent 0,714,273, with statement of matters that may be discussed, dated 03.06.02 (Jun. 3, 2002).

Communication from European Patent Office re European Patent 0,714,273, to Diehl, Glaeser, Hiltl & Partner, dated 29.04.02 (Apr. 29, 2002), re a withdrawal of representation.

Letter from C.R. Davies of the Office of Frank B. Dehn & Co. to European Patent Office, dated Oct. 8, 2002, re "European Patent 714 273 . . .—Opposed by S.C.A. Hygiene Products A.B." and enclosures.

Letter from Adrian Hayes of Boult Wade & Tennant to European Patent Office, dated Nov. 8, 2002, with Declaration of Ulf Stig Werner Ekwall, Opposition Document E6; together with letter from European Patent Office forwarding the same to C.R. Davies of the Office of Frank B. Dehn & Co., dated 11.11.02 (Nov. 11, 2002).

Decision Rejecting the Opposition of European Patent 714 273, by European Patent Office, together with minutes of the proceedings held Nov. 14, 2002, both dated 02.12.02 (Dec. 2, 2002).

Notice of Appeal filed Jan. 30, 2003, by Opponent SCA Hygiene Products AB, from decision rejecting opposition, together with letter from European Patent Office forwarding the same to C.R. Davies of the Office of Frank B. Dehn & Co., dated 10.02.03 (Feb. 10, 2003).

MECHANICAL FASTENING TAPES AND METHOD FOR THEIR CONSTRUCTION

CROSS REFERENCE TO RELATED APPLICATIONS

This is a continuation of application Ser. No. 08/442,065, filed May 16, 1995 now U.S. Pat. No. 6,406,467, which is a continuation of application Ser. No. 08/263,281, filed Jun. 21, 1994, and now abandoned, which is a continuation of application Ser. No. 08/148,130, filed Nov. 5, 1993, and now abandoned, which is a continuation-in-part of application Ser. No. 08/105,701, filed Aug. 17, 1993, and now abandoned. Said application Ser. No. 08/148,130 is also a continuation-in-part of application Ser. No. 07/906,016, filed Jan. 26, 1992, by Bruce M. Siebers, Gary L. Travis and Thomas W. Odorzynski, issued Jun. 7, 1994, as U.S. Pat No. 5,318,555; which is a continuation-in-part of application Ser. No. 07/628,251, filed Dec. 17, 1990, and now abandoned; and also a continuation-in-part of application Ser. No. 07/954,094, filed Sep. 30, 1992, by Thomas H. Roessler, Bruce M. Siebers, Robert L. Popp, and Charles R. Fallen, issued Apr. 4, 1995, as U.S. Pat. No. 5,403,302; which is a division of application Ser. No. 07/627,874, filed Dec. 13, 1990, issued Jan. 5, 1993, as U.S. Pat. No. 5,176,671; which is a continuation of application Ser. No. 07/287,746, filed Dec. 20, 1988, and now abandoned.

BACKGROUND OF THE INVENTION

The use of mechanical fastening means on disposable absorbent products, such as diapers, training pants, adult incontinent products, feminine care products, and the like, are well known. A common type of mechanical fastener employed on disposable absorbent products is a hook-and-loop type fastener in which a hook or hook-like element is provided which is adapted for releasably engaging with a loop or loop-like material. Such hook-and-loop type fasteners are also well known in the prior art.

While the use of mechanical hook-and-loop type fasteners on disposable absorbent products is known, such use has not become widespread. This is due, in part, to the increased cost of such hook-and-loop type fasteners relative to the more common adhesive tapes currently used on disposable absorbent products. An additional reason that hook-and-loop type fasteners have not been widely used on disposable absorbent products relates to the difficulty of forming such hook-and-loop type fasteners at the high speeds generally associated with the manufacture of disposable absorbent products. The process issues associated with the formation of such hook-and-loop type fasteners also affects the relative cost of such fasteners. The process difficulties associated with the hook-and-loop type fasteners relates not only to the formation of the specific hook-and-loop materials, but also to the attachment of the hook-and-loop materials to other elements to form a fastening tape suitable for use on disposable absorbent products. The hook-and-loop materials must be attached securely enough to the other elements of the fastening tape so as not to present a product safety issue. In order to render the use of hook-and-loop type fasteners on disposable absorbent products more feasible, it is desirable to provide improved fastening tapes comprising hook-and-loop materials and processes for the manufacture of such fastening tapes.

SUMMARY OF THE INVENTION

In one aspect, the present invention concerns a fastening tape for use on a disposable absorbent garment. The fastening tape has a width and a length, a first transverse edge and a second transverse edge. The fastening tape comprises a first substrate having a width and an interlocking material attached to said first substrate and extending the entire width of said fastening tape. The interlocking material is longitudinally spaced from both said first and second transverse edges of said fastening tape.

In another aspect, the present invention concerns a fastening tape for use on a disposable absorbent garment. The fastening tape has a width and a length, a first transverse edge and a second transverse edge. The fastening tape comprises a first substrate having a width and an interlocking material attached to said first substrate. The interlocking material has a width and a length and two longitudinal edges. The interlocking material is attached to said first substrate such that at least one of said longitudinal edges of said interlocking material is not directly attached to said first substrate.

In another aspect, the present invention concerns a fastening tape for use on a disposable absorbent garment. The fastening tape has a width and a length, a first transverse edge and a second transverse edge. The fastening tape comprises a first substrate having a width and an interlocking material attached to said first substrate. The interlocking material has a width and a length and two longitudinal edges. The interlocking material is attached to said first substrate with both adhesive and thermal bonds.

In another aspect, the present invention concerns a continuous process for manufacturing a fastening tape for use on a disposable absorbent garment. The process comprises the following steps: (1) providing a continuous length of an interlocking material having a width and traveling in a first direction; (2) attaching said interlocking material to a first substrate traveling in said first direction to form a composite; and (3) cutting said composite along a second direction to form fastening tapes suited for attachment to an absorbent garment, said second direction being substantially perpendicular to said first direction.

In a particularly preferred aspect, the present invention comprises a continuous process for manufacturing a fastening tape for use on a disposable absorbent garment. The process comprises the following steps: (1) providing a continuous length of an interlocking material having a width and traveling in a first direction; (2) attaching said interlocking material to a first substrate having a width and traveling in said first direction to form a composite; (3) slitting said composite along said first direction to form two slit composites; (4) attaching said two slit composites to a second substrate having a width and traveling in said first direction to form a tape assembly, said two split composites being laterally separated prior to attachment to said second substrate; (5) slitting said second substrate of said tape assembly along said first direction; and (6) cutting said tape assembly along a second direction to form fastening tapes, said second direction being substantially perpendicular to said first direction.

In another particularly preferred aspect, the present invention comprises a continuous process for manufacturing a fastening tape for use on a disposable absorbent garment. The process comprises the following steps: (1) providing two continuous lengths of an interlocking material having a width and traveling in a first direction, said two continuous lengths of interlocking material being laterally separated; (2) attaching said two continuous lengths of interlocking material to a first substrate having a width and traveling in said first direction to form a composite; (3) attaching said composite to a second substrate having a width and traveling in said first direction to form a tape assembly; (4) slitting said tape assembly in said first direction; and (5) cutting said tape assembly along a second direction to form fastening tapes, said second direction being substantially perpendicular to said first direction.

In another particularly preferred aspect, the present invention comprises a continuous process for manufacturing a fastening tape for use on a disposable absorbent garment. The process comprises the following steps: (1) providing two continuous lengths of an interlocking material having a width and traveling in a first direction, said two continuous lengths of interlocking material being laterally separated; (2) attaching said two continuous lengths of interlocking material to a first substrate having a width and traveling in said first direction to form a composite, said two continuous lengths of interlocking material being attached to said first substrate with both adhesive and thermal bonds; (3) attaching said composite to a second substrate having a width and traveling in said first direction to form a tape assembly; (4) slitting said tape assembly in said first direction; and (5) cutting said tape assembly along a second direction to form fastening tapes, said second direction being substantially perpendicular to said first direction.

DETAILED DESCRIPTION OF THE PREFERRED EMBODIMENTS

The present invention relates to a fastening tape suitable for use on disposable absorbent garments. The term "disposable absorbent garments" is intended to refer to any disposable garment intended to absorb discharged body fluids. Examples of disposable absorbent garments include diapers, adult incontinence products, training pants, feminine napkins, wound dressings, and the like. For ease of understanding, much of the following description will be made in terms of the use of the fastening tapes of the present invention on disposable diapers. Nonetheless, it is to be understood that the fastening tapes of the present invention are equally suited for use on any other disposable absorbent garment and that the bonding methods described herein are equally well suited for use in other applications such as in other aspects of the construction of disposable absorbent garments.

Figure 1:
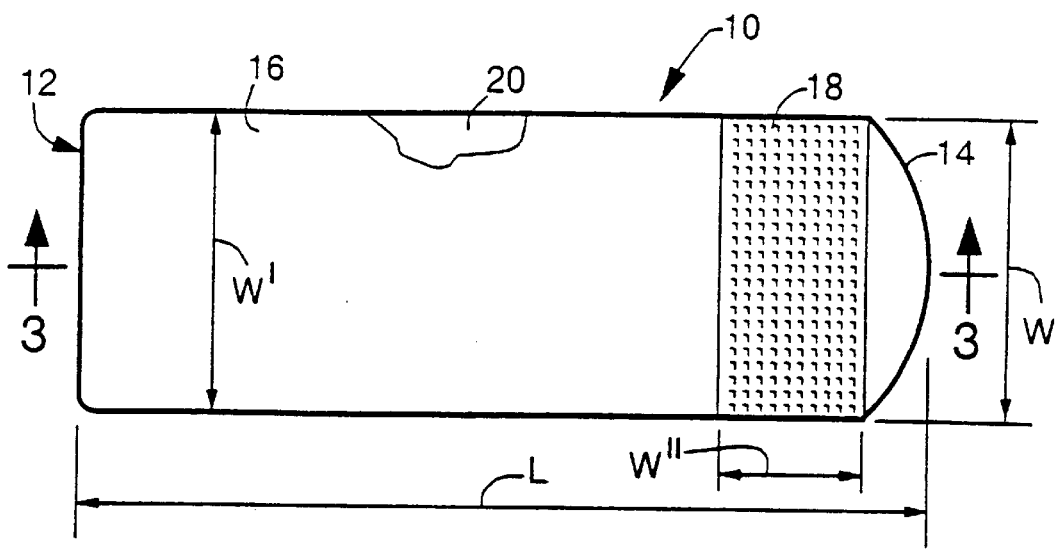
FIG. 1 is a plan view of a fastening tape according to the present invention.

In one aspect, the present invention refers to a fastening tape for use on disposable absorbent garments. The fastening tape can best be understood by reference to the figures wherein FIG. 1 illustrates a plan view of a fastening tape according to this aspect of the present invention. The fastening tape 10 has a length L and a width W. As used herein, reference to the length of a fastening tape is intended to refer to the dimension of the fastening tape generally perpendicular to the length of the disposable absorbent garment to which it is attached. The length of a disposable absorbent garment refers to that dimension of the garment which extends from a rear waistband area of the garment, through a crotch area of the garment, to an opposite waistband area of the garment. This generally corresponds to the machine direction of the garment during manufacture and the greatest planar dimension of the product. The width of the fastening tape refers to the dimension of the fastening tape generally perpendicular to the length thereof.

The fastening tape 10 defines a first transverse edge 12 and a second transverse edge 14. The fastening tape 10 comprises a first substrate 16 having a width W'. In the illustrated embodiment, the width W' of the first substrate 16 corresponds to the overall width W of the fastening tape 10. An interlocking material 18 is attached to the first substrate 16 and extends the entire width W of the fastening tape 10. The interlocking material is longitudinally spaced from both the first transverse edge 12 and the second transverse edge 14. The interlocking material has a width W" extending along the length direction of the fastening tape and a length perpendicular to the width W".

As used herein, reference to an interlocking material is intended to refer to a material which is adapted to mechanically interlock with a second material. In the illustrated embodiment, the interlocking material is either the hook or the loop portion of a hook-and-loop fastener. Hook-and-loop fasteners are known to those skilled in the art. A hook-and-loop fastener generally comprises a hook material and a loop material. The hook material generally comprises a base sheet material from which stemlike projections extend. One end of the stemlike projection is attached to the base sheet material, while the other end of the stemlike projection defines a hook, or hook-like structure, which is adapted to interlock with a loop or loop-type material. The loop or loop-type material generally comprises a woven or nonwoven material defining individual loops of material which can interlock with the hook or hook-like material. Other interlocking materials include cohesive materials, snaps, and the like.

Exemplary of a hook material suitable for use in the present invention is that obtained from Velcro Group Company, Manchester, N.H., under the trade designation CFM-22 and CFM-15. Suitable hook materials generally comprise from about 300 to about 1000 hooks per square inch (about 46 to about 155 hooks per square centimeter), preferably from about 700 to about 900 hooks per square inch (about 108 to about 140 hooks per square centimeter). The hooks suitably have a height of from about 0.015 inch (0.038 centimeter) to about 0.050 inch (0.127 centimeter), preferably of from about 0.025 inch (0.0635 centimeter) to about 0.035 inch (0.0889 centimeter).

Exemplary of a loop material suitable for use in the present invention is that obtained from Guilford Mills, Inc., Greensboro, N.C., under the trade designation Style 19902 or Style 30020. A suitable loop is a fabric of a raised loop construction, stabilized through napping and thermosetting such that the loops are erect from the base material. The fabric may be a two bar warp knit construction having from 21 to 41 courses per inch (8.27 to 16.4 courses per centimeter) and from 26 to 46 wales per inch (10.24 to 18.1 wales per centimeter), preferably of polyester yarn, in which 15–35 percent of the yarn is composed of yarn having about 15 or less filaments and having a yarn denier (d) within the range of about 15–30 d. In addition, about 65–85 percent of the yarns are those having 1–30 individual filaments therein and having a yarn denier within the range of about 30–50 d. The caliper is 0.010 to 0.040 inch (0.0254 to 0.1 centimeter) and basis weight from 1.0 to 3.0 ounces per square yard. Suitable loop materials are shown, for example, in U.S. Pat. No. 5,019,073 issued May 28, 1991, to Roessler et al., the disclosure of which is incorporated by reference herein.

While the interlocking material attached to the first substrate may be either a hook material or a loop material, it is generally preferred that the interlocking material comprise a hook material. Those skilled in the art will appreciate that the second interlocking material, with which the interlocking material 18 is intended to interlock, will be positioned on the disposable absorbent garment such that the fastening tape 10 can be utilized to attach the disposable absorbent garment about the waist of a wearer. In general, the fastening tape 10 will be attached to the rear periphery of the disposable absorbent garment, and the second interlocking material will be attached to the outer surface of the disposable absorbent garment, near a front edge of the garment. This aspect of the invention will be described in greater detail below. Alternatively, the fastening tape 10 may be attached to the front periphery of the disposable absorbent garment, and the second interlocking material may be, attached to the outer surface of the disposable absorbent garment, near a rear edge of the garment.

Figure 2:
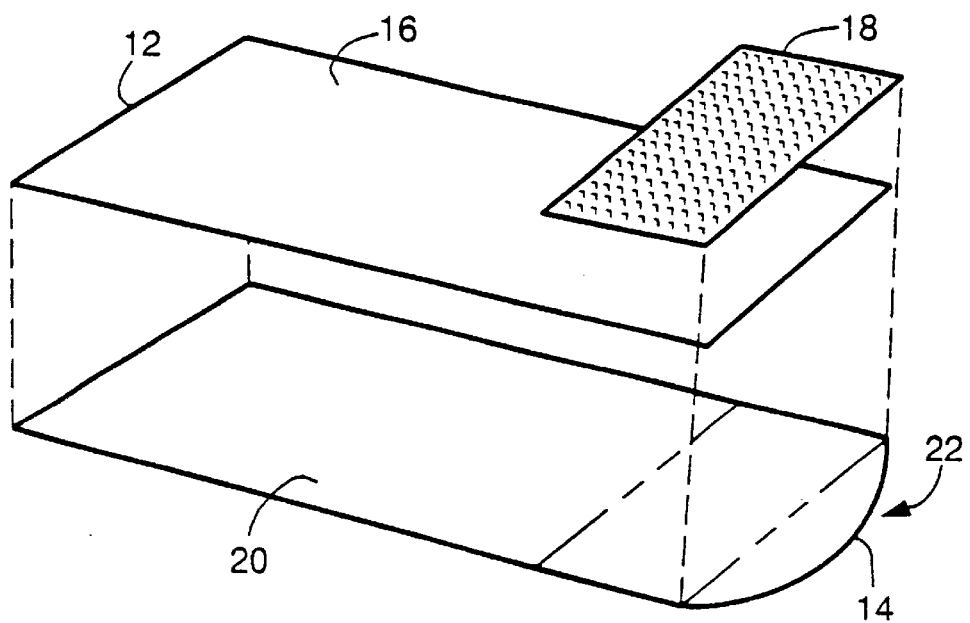
FIG. 2 illustrates an exploded perspective view of the fastening tape illustrated in FIG. 1.

The fastening tape of the present invention may be formed from first substrate 16 and interlocking material 18. In the particular embodiment illustrated in FIG. 1, the fastening tape 10 further comprises a second substrate 20 to which the first substrate is attached. This aspect of the invention can best be understood by reference to FIG. 2 which is an exploded perspective view of the fastening tape 10 illustrated in FIG. 1. As can be seen from reference to FIG. 2, the first substrate 16 has a length which is less than the length of the second substrate 20, but has a width which is equal to the width of the second substrate 20. The length of the second substrate 20 which extends beyond the length of the first substrate 16 defines a tab generally designated by the numeral 22 which, in use, functions as a finger tab, allowing a user to easily remove the interlocking material 18 from an interlocked relationship with a second interlocking material. Further, tab 22 serves to prevent skin irritation which could otherwise be caused by the edges of the interlocking material 18.

Figure 4A:
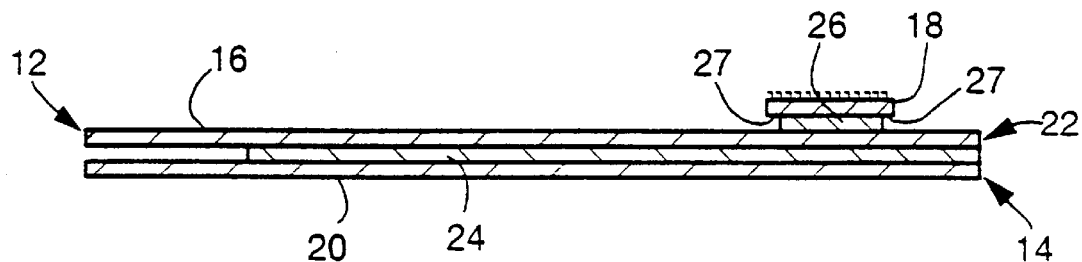
FIG. 4A illustrates a first alternative embodiment of a fastening tape according to the present invention.
Figure 4B:
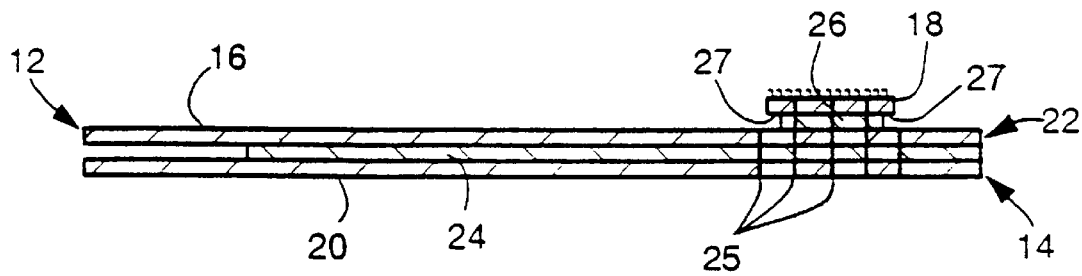
FIG. 4B illustrates a second alternative embodiment of a fastening tape according to the present invention.

It is to be understood that the first and second substrates may have a wide variety of configurations relative to one another. For example, the first substrate 16 and the second substrate 20 may have the identical configuration (FIGS. 4A and 4B). Alternatively, the second substrate may have a length or a width which is less than or greater than the first substrate 16.

Any flexible material having the required physical strength to perform a fastening function as described herein is believed suitable for use as the first and/or second substrate material. Examples of materials suitable for use as the first and second substrate include thermoplastic or thermosetting films, such as polyolefin films, polyurethane films, and the like; nonwoven materials such as meltblown or spunbonded polyolefins; woven materials; nonwoven composites; nonwoven/film composites; and the like.

Any method capable of attaching the first and second substrate to one another, and/or the first interlocking material to the first substrate, is believed suitable for use in the present invention.

For example, the materials may be attached together by hot or cold melt adhesives, thermal bonding (including ultrasonic bonding), sewing, combinations of these methods, and the like. In one preferred embodiment of the present invention the interlocking material is attached to the first substrate with both adhesive and thermal bonds.

Figure 3:
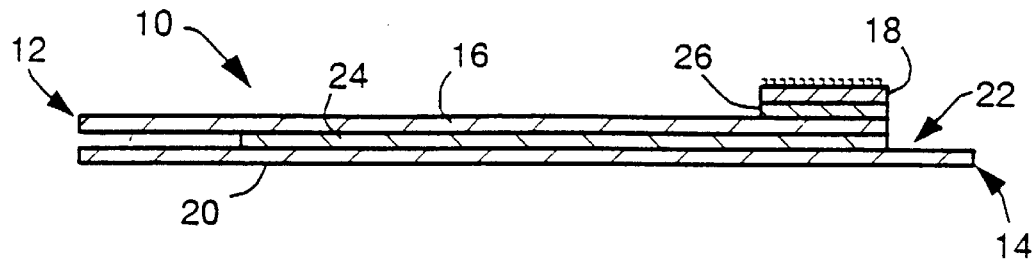
FIG. 3 is a cross-sectional view of the fastening tape of FIG. 1 taken along line 3—3 of FIG. 1.

FIG. 3 illustrates a cross-sectional view taken along line 3—3 of FIG. 1. FIG. 3 illustrates an embodiment wherein the first substrate 16 and second substrate 20 are adhesively bonded together by adhesive layer 24. Similarly, interlocking material 18 is bonded to the first substrate 16 by an adhesive material 26. Those skilled in the art will recognize suitable adhesive materials for use in forming adhesive layers 24 and 26. Exemplary of adhesive materials suitable for use as adhesive layers 24 and 26 are those commercially available from Findley Adhesives, Inc., Wauwatosa, Wis., under the trade designation H-2096. As can be seen from reference to FIG. 3, the first and second substrates are unattached in an area in which they overlap. That is, adhesive layer 24 does not extend all the way to transverse edge 12 of the fastening tape 10. Accordingly, a portion of the first substrate 16 and the second substrate 20 will not be adhered to one another at longitudinal end 12.

The adhesive layer 26 may be coextensive with the interlocking material 18. Alternatively, the adhesive layer 26 may cover less than the entire interlocking material 18. Specifically, the adhesive layer 26 may not extend to one or more longitudinal edges of the interlocking material 18 relative to the width (W") of the interlocking material 18. Thus, the longitudinal edges of the interlocking material are not directly attached to the first substrate. This aspect of the invention can be seen from reference to FIG. 4A wherein the adhesive layer 26 is shown as having a width which is less than the width (W") of the interlocking material 18. By having adhesive layer 26 cover less than the entire interlocking material 18, unattached edges 27 are formed between interlocking material 18 and the first substrate 16. In one preferred embodiment, the adhesive layer 26 comprises a plurality of beads of adhesive.

Beads of adhesive have been found to provide better adhesion of the interlocking material 18 to the first substrate 16.

The presence of the unattached edges 27 have been found to lessen the likelihood of interlocking material 18 being separated from the fastening tape 10. Specifically, in the embodiment illustrated in FIG. 4A, the presence of the unattached edges 27 is more likely to cause separation of the interlocking material 18 from the fastening tape 10 to occur through separation of the interlocking material 18 and the adhesive layer 26. When the unattached edges 27 are absent (FIG. 3), separation of the interlocking material 18 from the fastening tape 10 is more likely to occur through separation of the first substrate and the second substrate and tearing of the first substrate. As a general rule, the force required to separate the interlocking material 18 from the adhesive layer 26 is greater than the force required to separate the first substrate from the second substrate.

Further, the presence of unattached edges 27 have been found to improve the performance of the hook and loop fastening system. Specifically, the presence of unattached edges 27, particularly on the finger tab side of the interlocking material 18, has been found to cause initial separation of the interlocking (hook) material 18 from the loop material to occur through a shear mode (force generally parallel to plane of interlocking) rather than a peel mode (force generally perpendicular to plane of interlocking). Those skilled in the art will recognize that the force required to separate a hook and loop material through a shear mode is generally greater than the force required to separate the same materials through a peel mode.

The unattached edges 27 generally have a width of from about 5 percent to about 35 percent, preferably of from about 10 percent to about 25 percent of the width (W") of the interlocking material 18. The interlocking material 18 and adhesive layer 26 may form unadhered edges around the entire periphery of the interlocking material 18 or only around a portion of its periphery.

FIG. 4B illustrates a second, preferred, alternative embodiment of the present invention. FIG. 4B is identical to FIG. 4A with the exception that FIG. 48 further comprises thermal bonds 25. Thus, in the embodiment illustrated in FIG. 4B the interlocking material 18 is attached to the first substrate 16 by both adhesive layer 26 and thermal bonds 25, that is, by both adhesive and thermal bonds. Further, the first substrate 16 is attached to the second substrate 20 by both adhesive layer 24 and thermal bonds 25.

Applicants have discovered that attachment of the interlocking material 18 to the first substrate 16 by both adhesive and thermal bonds has been found to produce a system of attachment that possesses both good shear adhesion (creep mode) and good peel adhesion (dynamic). Specifically, the adhesive bond is as described above. As stated above the adhesive bond possesses excellent peel adhesion. However, under certain conditions, such as elevated temperature, the shear adhesion of the adhesive bond alone has been found to be less than desired in some instances. Applicants have discovered that the use of thermal bonds in addition to the adhesive bonds has been found to produce a system of attachment that possesses both good shear and good peel adhesion. Applicants hypothesize, without intending to be bound thereby, that the presence of the adhesive bonds contribute significantly to the peel adhesion of the system while the presence of the thermal bonds contributes significantly to the shear adhesion of the system.

As used herein, reference to "thermal" bonds is intended to refer to bonds formed as a result of the application of energy which causes localized heating. Accordingly, reference to thermal bonds includes bonds formed by the application of electromagnetic radiation as well as the application of ultrasonic energy.

In a preferred embodiment, the thermal bonds are ultrasonic bonds. Those skilled in the art will recognize methods suitable for forming ultrasonic bonds. Equipment and methods of ultrasonic bonding are, for example, illustrated in U.S. Pat. Nos. 5,110,403 issued May 5, 1992, to Ehlert; and 5,096,532, issued Mar. 3, 1992, in the name of Neuwirth et al. The ultrasonic bonds are desirably sufficient to cause the interlocking material 18 and the first substrate 16 to melt and flow together to affect the bonding function.

Any pattern of thermal bonding is believed suitable for use in the present invention. Suitable bonding patterns include, individual, separated areas of bonding such as circles, squares, triangles, diamonds, and the like; lines; bars; sine waves; dashes; and the like. Those skilled in the art will recognize that when the interlocking material 18 is the hook material of a hook-and-loop fastener, that formation of such thermal bonds may destroy the functionality of the individual hooks present in the area of thermal bonding. Accordingly, it is generally desired to design the bonding pattern such that is destroys the functionality of as few hooks as possible. For this reason the thermal bonding covers from about 1 to about 20, alternatively from about 1 to about 10, alternatively from about 1 to about 5 percent of the surface area of the interlocking material (also referred to as bond area). Accordingly, when it is desired to space the thermal bonding over the entire surface area of the interlocking material, it may be desired to employ individual thermal bonds having a surface area of from about 0.0001 to about 1.5 square centimeters, alternatively of from about 0.001 to about 0.013 square centimeters.

In some instances it may be possible to see a synergistic effect between the adhesive and thermal bonds. Applicants believe this is most likely to occur when the thermal bonding is in a continuous pattern such as a line or wave and when the total bond area is approximately 7 percent or greater, up to about 20 percent.

In some cases, it may be desirable to design the interlocking material so that the thermal bonds do not destroy the functionality of the hooks. For example, marginal portions of base material, which are free from hooks, could be provided on the interlocking material and the thermal bonding could occur in those marginal portions. Alternatively, discrete hook free areas could be provided across the surface area of the interlocking material and the thermal bonds could be located in those hook free areas.

In one preferred embodiment, the thermal bonds are formed by ultrasonic bonding and are in the form of individual, circular bonds having a diameter of about 0.064 centimeter and covering about 2 percent of the surface area of the interlocking material. The bonds are generally evenly spaced over the surface of the interlocking material. Such bonds are suitably formed by tapered pins having a base diameter of about 0.064 centimeter, taper of about 15 degrees and a height of about 0.15 centimeter. The pins are located on the anvil of an ultrasonic bonding apparatus which functions together with an ultrasonic horn to produce the thermal bonds. In order to further protect the functionality of hooks present on the interlocking material, it is preferred that the anvil of the ultrasonic bonding apparatus contact the interlocking material and the horn of the ultrasonic bonding apparatus contact the first substrate. Further, it is preferred that the pins or other raised area defining the bonding pattern have a height which is great enough to prevent damaging the hook members to an unacceptable degree. Specifically, it is generally desired that the pins or other raised area defining the bonding pattern have a height which is greater than the total thickness of the material being thermally bonded.

In the embodiment illustrated in FIGS. 4A and 4B, the first substrate 16 and the second substrate 20 have the same length. Adhesive layer 24 extends between the first and second substrates out to the second transverse edge 14 of fastening tape 10 but does not extend to the first transverse edge 12.

In the embodiment illustrated in FIGS. 3, 4A and 4B, fastening tape 10 is intended to be attached to a disposable absorbent garment by attaching the unadhered portion of the first substrate 16 to the inner surface of a disposable absorbent garment and attaching the unadhered portion of the second substrate 20 to the outer surface of the disposable absorbent garment. That is, the absorbent garment is sandwiched between the unadhered portions of the first substrate 16 and the second substrate 20. This aspect of the present invention is explained in greater detail below in connection with FIGS. 11 and 12.

Naturally, other methods of attaching the fastening tape 10 to the disposable absorbent garment are possible. For example, the first and second substrates could be adhered together along their entire length. The fastening tape could then be attached to the inner or outer surface of the garment. Alternatively, the fastening tape 10 could be attached to the disposable absorbent garment between individual components of the garment. These alternative methods of attachment apply with equal force to a fastening tape comprising a single, first substrate and no second substrate.

The interlocking material 18 is desirably longitudinally spaced from both the first transverse edge 12 and the second transverse edge 14 of the fastening tape 10. It is desired that the interlocking material be spaced from each transverse edge by a distance of at least about 2 millimeters, preferably of at least about 8 millimeters, and most preferably of at least about 16 millimeters. In this manner, the finger tab 22 may be provided. As a general rule, the first interlocking material 18 will be positioned more closely toward the second transverse edge 14 than the first transverse edge 12. Nonetheless, when the interlocking material 18 is relatively soft, the interlocking material may be located at the first or second transverse edge of the fastening tape.

Figure 5:
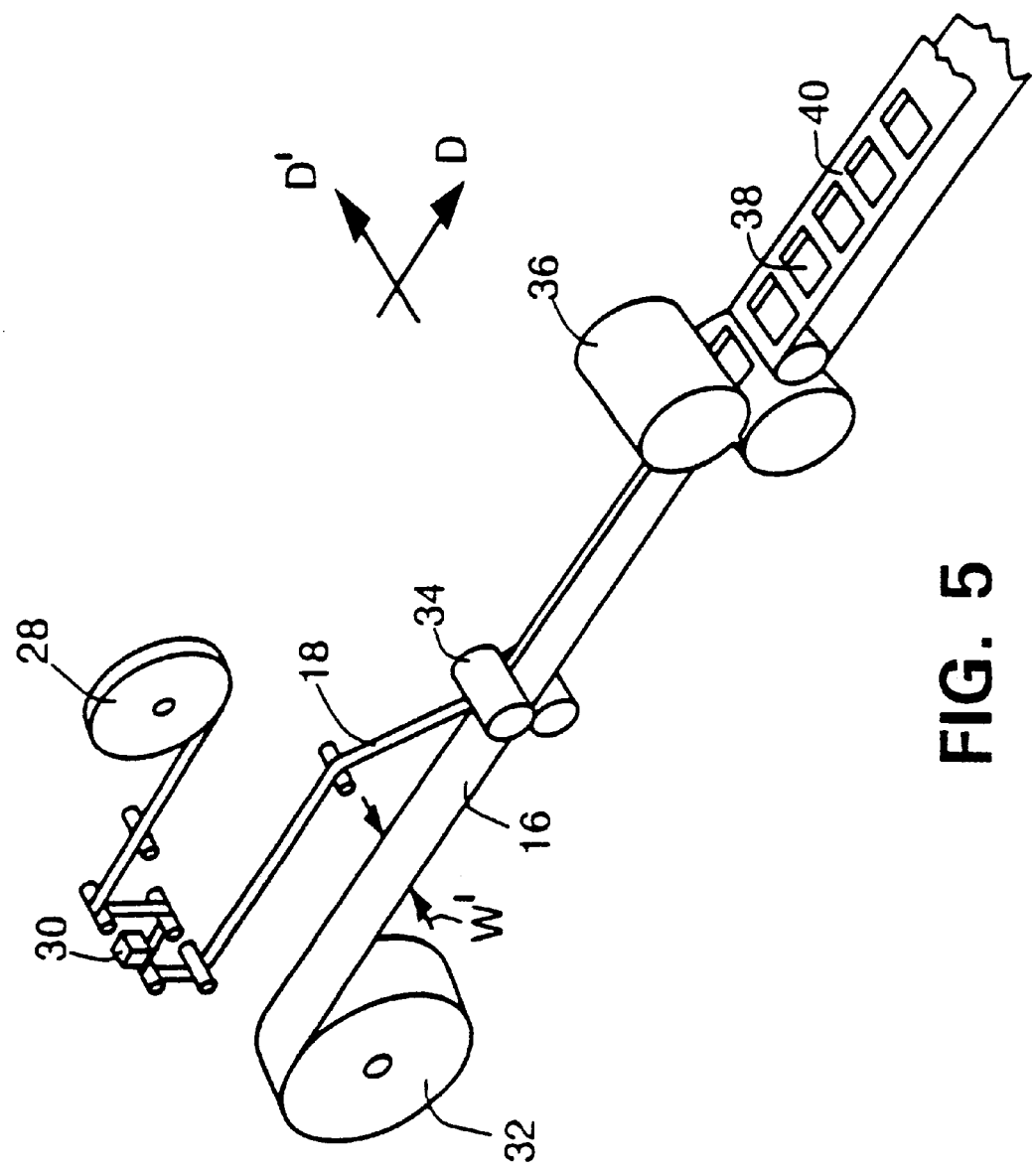
FIG. 5 schematically illustrates a first embodiment of the process of the present invention.

In another aspect, the present invention concerns a process for manufacturing a fastening tape for use on a disposable absorbent garment. The process can best be understood by reference to the drawings wherein FIG. 5 illustrates a schematic view of a process according to the present invention. A generally continuous length of an interlocking material 18 is provided. The interlocking material 18 is provided from supply roll 28. The continuous length of interlocking material has a width and is traveling in a first direction D. The width of the interlocking material is measured in a direction generally perpendicular to direction D. In the embodiment illustrated in FIG. 5, a hot melt glue is applied to the interlocking material by applicator 30. A first substrate 16 is provided from supply roll 32. The first substrate 16 has a width W' and is traveling in the first direction D. The interlocking material 18 is attached to the first substrate 16, near one longitudinal edge of the first substrate, as a result of the adhesive applied to the interlocking material by applicator 30. A pair of nip rollers 34 ensures adhesive contact between the interlocking material 18 and the first substrate 16. The attachment of the interlocking material to the first substrate forms a composite.

Those skilled in the art will recognize that any means capable of joining the first interlocking material to the first substrate is suitable for the present invention. For example, in addition to adhesive attachment, it is possible to thermally bond (including ultrasonic bonding), or sew the interlocking material to the first substrate. Again, in a preferred embodiment, the first interlocking material is joined to the first substrate by both adhesive and thermal bonds. Similarly, applicator 30 may comprise a slotcoater, spray applicator, bead applicator, or curtain applicator.

The composite of interlocking material 18 and first substrate 16 is then cut by cutter 36 to form individual fastening tapes 38. Cutter 36 cuts the composite in a second direction D' substantially perpendicular to the first direction D. The fastening tapes 38 are then conveyed on conveyer 40 to a location for application to a disposable absorbent garment.

Those skilled in the art will recognize that cutter 36 may comprise rotary cutters, air knives, thermal knives, pinch cutters, ultrasonic cutters, lasers, and the like.

Conveyor 40 may comprise a conveying belt, vacuum drum, transfer layers, gripper fingers, and the like.

Figure 6:
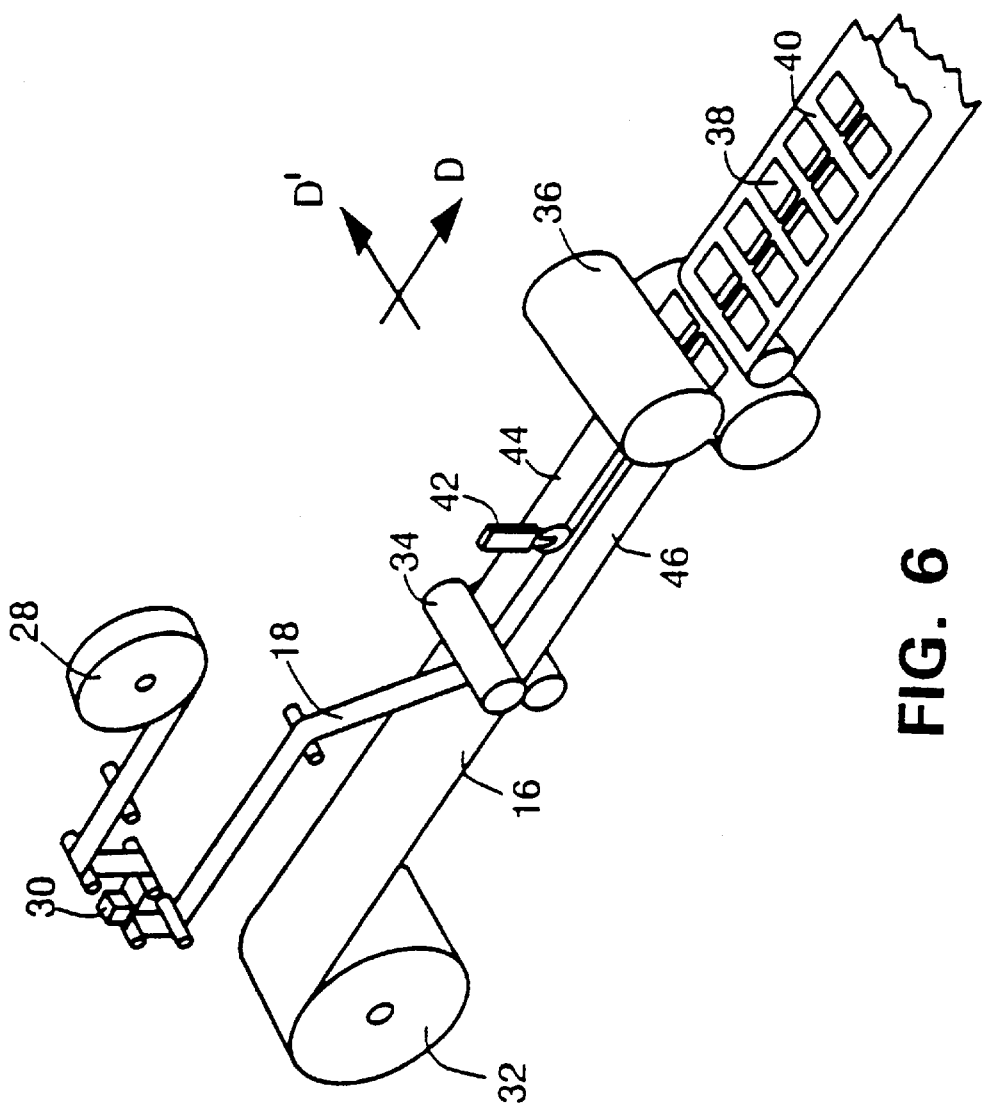
FIG. 6 schematically illustrates a second embodiment of the process of the present invention.

A second embodiment of the process according to the present invention is illustrated in FIG. 6. The process illustrated in FIG. 6 is substantially identical to the process illustrated in FIG. 5 with the exception that the interlocking material 18 is applied to the first substrate 16 generally in the center of the first substrate 16. After forming the composite of the interlocking material 18 and first substrate 16, the composite is slit by slitter 42 to form two slit composites 44 and 46. Each slit composite 44 and 46 comprises the first substrate 16 and the interlocking material 18. As in the process illustrated in FIG. 5, cutter 36 cuts the slit composites 44 and 46 along a second direction D' substantially perpendicular to the first direction D to form fastening tapes 38. Conveyor 40 conveys fastening tapes 38 to the location at which they are to be joined to a disposable absorbent garment.

As can be appreciated from reference to FIG. 6, by slitting the composite to form two slit composites 44 and 46 prior to cutting along the second direction, each cut along the second direction made by cutting means 36 may form two fastening tapes. Obviously, if it is desired to form fastening tapes having the same general dimensions as those tapes illustrated in FIG. 5, the first substrate 16 and the interlocking material 18 will need to have starting widths twice that of the interlocking material 18 and first substrate 16 illustrated in FIG. 5.

The process illustrated in FIG. 6 may be preferred over that illustrated in FIG. 5 since it forms two fastening tapes for each cut of cutter 36. Those skilled in the art will appreciate that disposable absorbent garments on which the fastening tapes of the present invention can be utilized generally utilize at least two of such fastening tapes. Thus, each cut of cutter 36 can form two fastening tapes which may be sufficient to provide all of the fastening tapes for a specific disposable absorbent garment.

Figure 7:
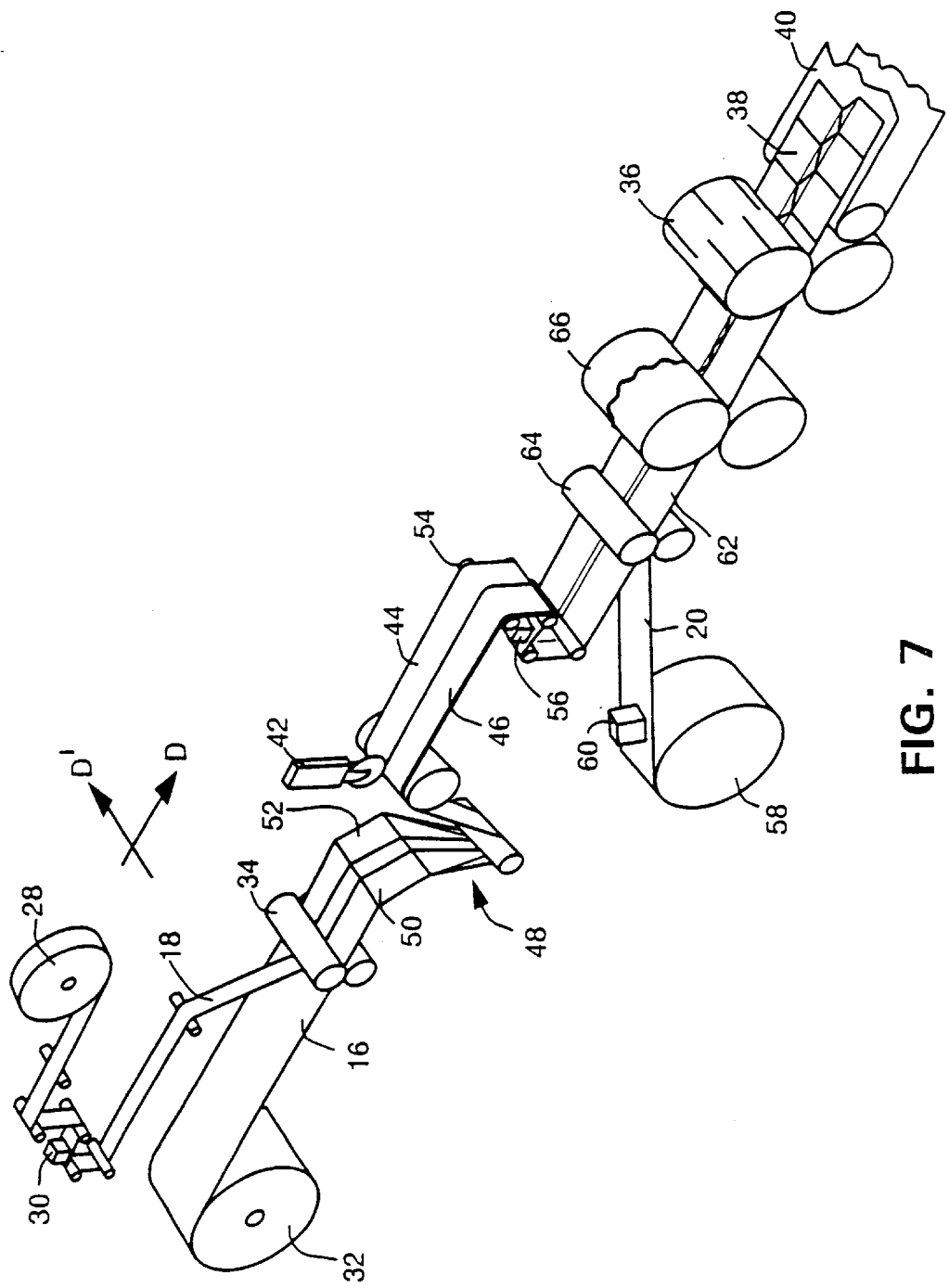
FIG. 7 schematically illustrates a third embodiment of the process of the present invention.

FIG. 7 illustrates a particularly preferred process according to the present invention.

According to the process illustrated in FIG. 7, the interlocking material 18 is again supplied from supply roll 28. Applicator 30 applies adhesive to the interlocking material which is then adhered to the first substrate 16 supplied from supply roll 32 to form a composite. The interlocking material 18 is applied to first substrate 16 generally at the center of substrate 16. Nip rollers 34 ensures adhesive bonding between the first substrate 16 and the interlocking material 18. At folding area 48, the longitudinal edges 50 and 52 of the first substrate 16 are folded on top of the composite so that the edges 50 and 52 are in contact with the planar surface of the first substrate 16 to which the interlocking material 18 is attached. The composite is then slit by slitter 42 to form two slit composites 44 and 46. The two slit composites 44 and 46 are then laterally spaced along direction D' by spreader 54. The two slit composites continue to travel in the first direction D.

An adhesive is applied to the two slit composites by adhesive applicator 56. A second substrate 20 traveling in the first direction D is provided by supply roll 58. An adhesive is applied to the second substrate 20 by adhesive applicator means 60. The two slit composites 44 and 46 are then attached to the second substrate while the two slit composites are in a laterally spaced condition. In this manner, a portion of the second substrate separates the two slit composites. It is this portion of the second substrate which forms the finger tab 22 illustrated in FIGS. 1–3. Attachment of the slit composites 44 and 46 to the second substrate 20 forms a tape assembly 62. The tape assembly 62 passes through nip roller 64 to ensure adhesive sealing of the first substrate to the second substrate.

Slitter 66 then slits the second substrate of the tape assembly along the first direction D in that portion of the second substrate which separates the two slit composites 44 and 46 to form two slit tape assemblies. In a preferred embodiment, the second substrate is slit in the first direction along an interlocking pattern such as a sinusoidal wave pattern. The slit tape assemblies are then cut, by cutter 36, along a second direction D' to form fastening tapes 38. Specifically, the first substrate 16 and interlocking material 18 are cut along the second direction D' while the second substrate 20 is simultaneously cut along said second direction at a location adjacent the location at which the first substrate is cut. The second direction D' is again substantially perpendicular to the first direction. The fastening tapes 38 are then conveyed by conveyor 40 to the point at which they are applied to a disposable absorbent garment.

In a preferred embodiment, the interlocking material 18 is attached to the first substrate with both adhesive and thermal (ultrasonic) bonds. Those skilled in the art would recognize modifications necessary to the process illustrated in FIG. 7 to product a fastening tape wherein the interlocking material is adhered to the first substrate with both adhesive and thermal (ultrasonic) bonds. For example, an ultrasonic bonding apparatus such as that described above may be included in the process immediately after nip rollers 34, nip roll 64 or slitter 66.

Folding area 48 suitably contains folding boards, plows, and the like, to effectuate the described folding. Spreader 54 suitably comprises bowed rollers, bowed bars, angled rollers, spiral rollers, or the like. The cutter 66 suitably comprises a rotary cutter, water cutter, laser cutter, and the like. The adhesive applied by applicators 30, 56 and 60 are suitably hot melt adhesives which adhesives and adhesive applicator systems are commercially available from Nordson Corporation, Westlake, Ohio; Spraymation, Inc., Ft. Lauderdale, Fla.; Accumeter Laboratories, Inc., Marlboro, Mass.; Findley Adhesives, Inc., Wauwatosa, Wis.; and J&M Laboratories, Inc., Gainesville, Ga. Of course, other methods of attachment can be substituted for the described adhesive attachment.

Figure 8A:
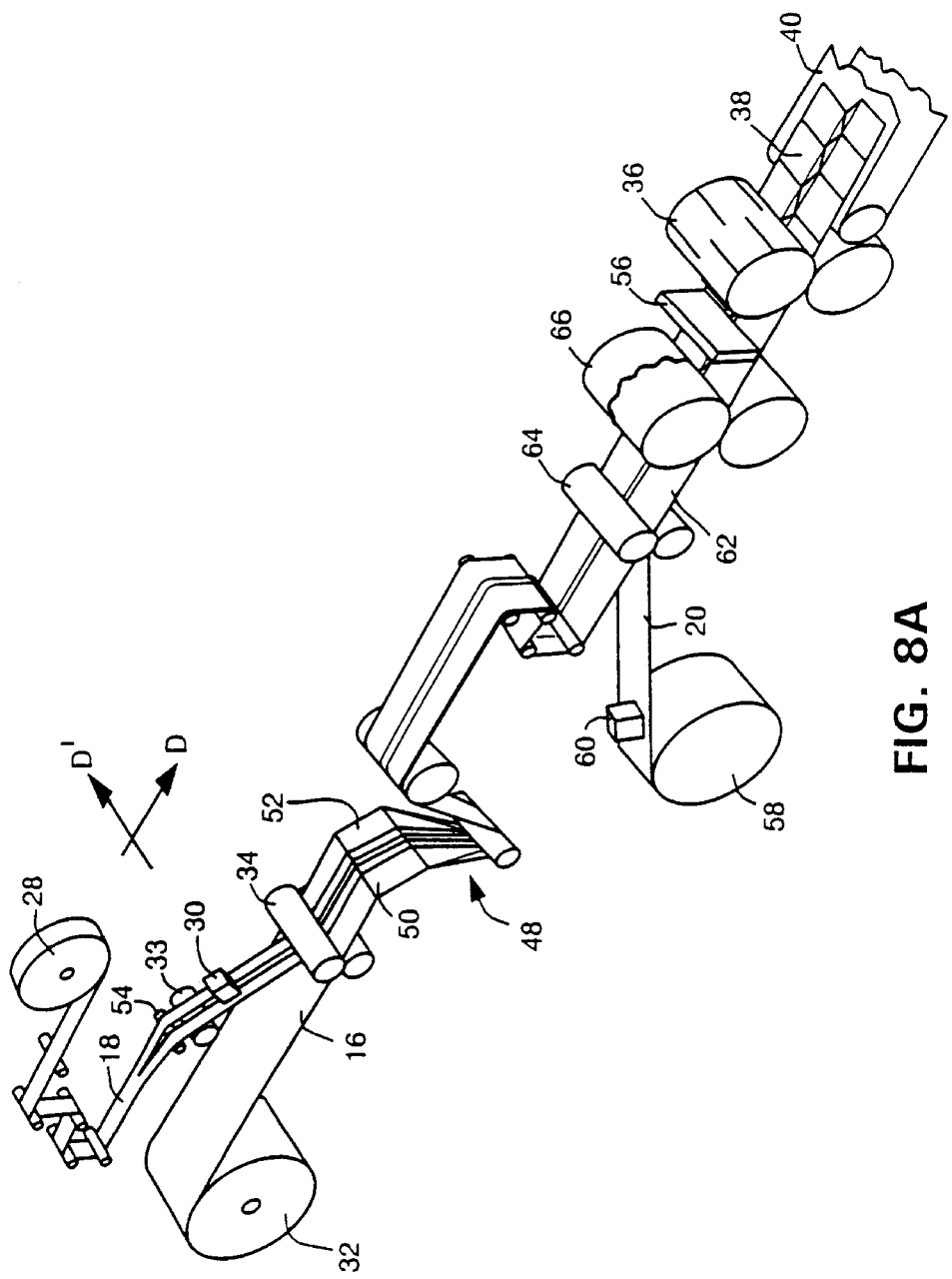
FIG. 8A schematically illustrates a fourth embodiment of the process of the present invention.

FIG. 8A illustrates another preferred process according to the present invention. According to the process illustrated in FIG. 8A, an interlocking material 18 is again supplied from supply roll 28. The interlocking material is formed with a line of weakness along its length. The line of weakness is, for example, free of hooks and has a base which is thinner than the surrounding material. This allows the interlocking material 18 to be split into two pieces. The two pieces of interlocking material are split and laterally spaced along direction D' by spreader 54. In the illustrated embodiment, spreader 54 comprises a contoured roll. Both pieces of the interlocking material 18 are then passed over heated roll 33 and have adhesive applied thereto by applicator 30. The two pieces of interlocking material are then adhered to a first substrate 16 supplied from supply roll 32 to form a composite which is compressed by nip rollers 34 to ensure adhesive bonding. The width of the two pieces of interlocking material is less than the width of the first substrate. At folding area 48, the longitudinal edges 50 and 52 of the first substrate 16 are folded on top of the composite comprising the first substrate 16 and the interlocking material 18. The folding occurs so that the edges 50 and 52 are in contact with a planar surface of the first substrate 16 and so that the first substrate 16 covers the exposed surface of interlocking material 18. A second substrate 20 traveling in the first direction D is provided by supply roll 58. An adhesive is applied to the second substrate 20 by adhesive applicator means 60. The composite of the first substrate 16 and interlocking material 18 is then attached to the second substrate. In this manner, a portion of both the first and second substrates separates the two pieces of interlocking material 18. It is these portions of the first and second substrates which form the finger tab illustrated in FIG. 4A. Attachment of the composite of the first substrate 16 and interlocking material 18 to the second substrate 20 forms a tape assembly 62. The tape assembly 62 passes through nip roller 64 to ensure adhesive sealing of the first substrate to the second substrate.

Slitter 66 then slits the first and second substrate of the tape assembly along the first direction D in that portion of the first and second substrates which separate the two pieces of interlocking material 18 to form two slit tape assemblies. In a preferred embodiment, the first and second substrates are slit in the first direction along a sinusoidal wave pattern. Adhesive applicator 56 then applies an adhesive to the slit tape assemblies. This adhesive will serve to attach the fastening tapes to the disposable absorbent product. The slit tape assemblies are then cut, by cutter 36, along a second direction D' to form fastening tapes 38. The second direction D' is substantially perpendicular to the first direction. The fastening tapes 38 are then conveyed by conveyor 40 to the point at which they are applied to a disposable absorbent product.

Figure 8B:
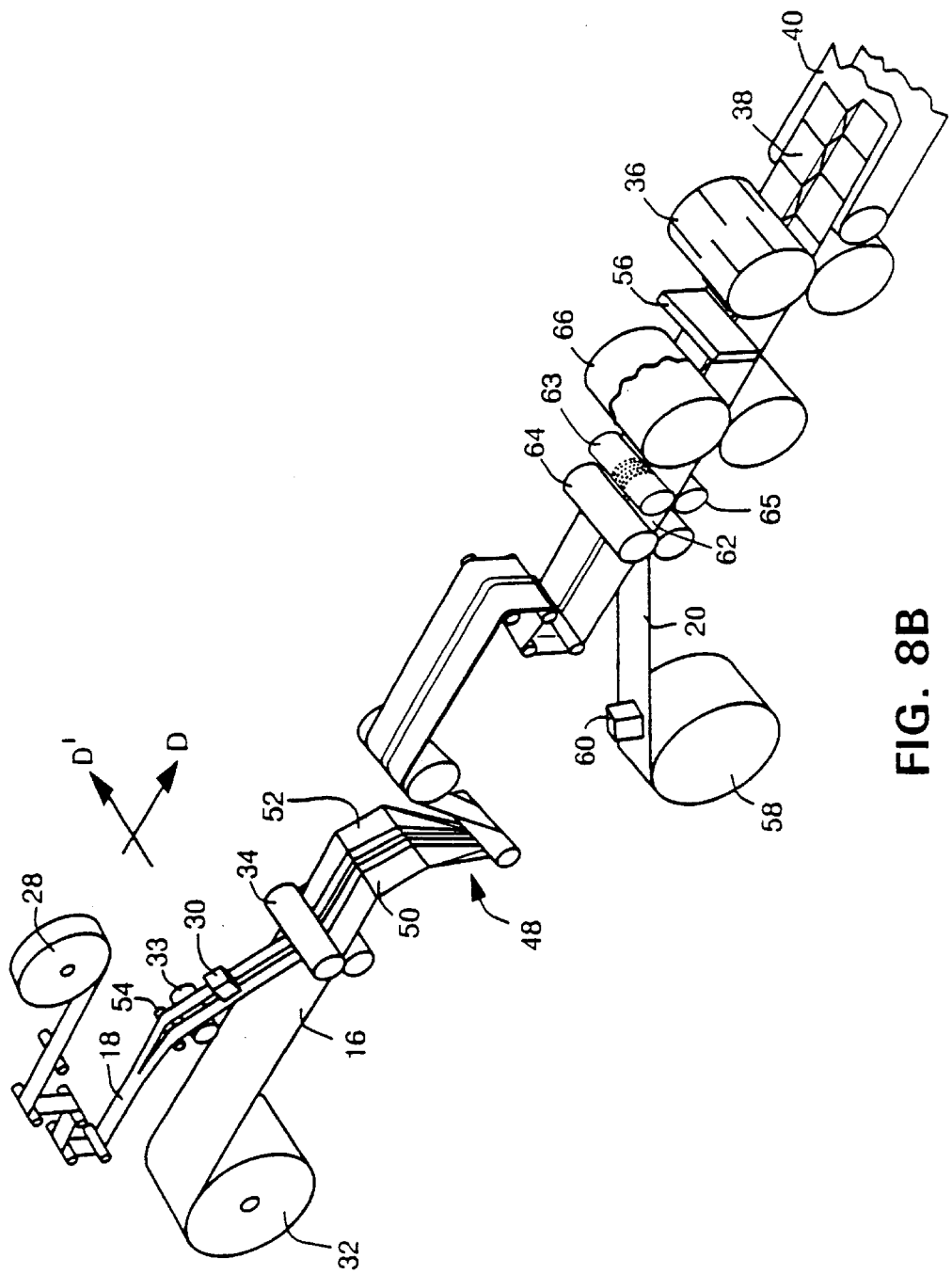
FIG. 8B schematically illustrates a preferred embodiment of the process illustrated in FIG. 8A.

FIG. 8B illustrates an embodiment of the process illustrated in FIG. 8A wherein the interlocking material 18 is attached to the first substrate with both adhesive and thermal (ultrasonic) bonds. Specifically, the process illustrated in FIG. 8B is identical to the process illustrated in FIG. 8A except that the process further comprises rotary ultrasonic anvil 63 and rotary ultrasonic horn 65. As can be seen from reference to FIG. 8B, the pattern of ultrasonic bonding does not cover the entire surface of the tape assembly 62 but is generally confined to the area consisting of the two pieces of the interlocking material, the area slightly beyond the outer edges of the interlocking material, and the area separating the two pieces of interlocking material. Further, the process illustrated in FIG. 8B differs from that illustrated in FIG. 8A in that the first substrate is folded at folding area 48 such that the first substrate 16 does not cover the interlocking material 18 and, in fact, stops about 0.125 inch short of the interlocking material. This is illustrated in greater detail in FIG. 9B.

Figure 9A:
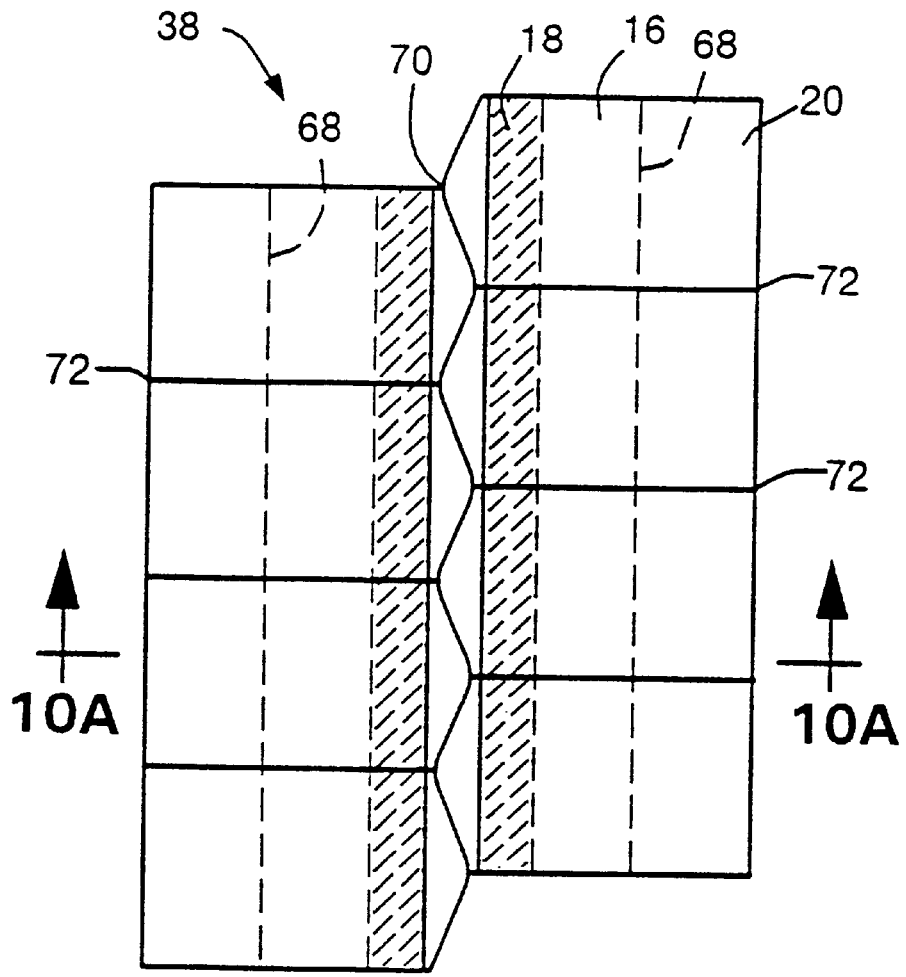
FIG. 9A is a plan view of fastening tapes manufactured by the process illustrated in FIG. 8A.
Figure 10A:
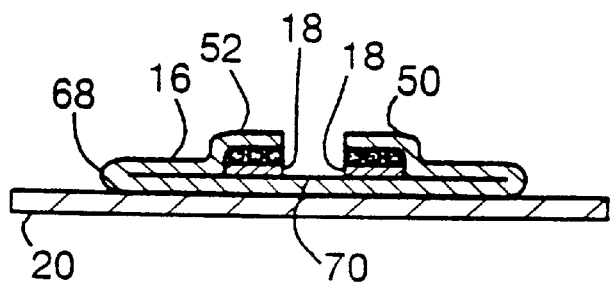
FIG. 10A is a cross-sectional view taken along line 10A—10A of FIG. 9A.
Figure 9B:
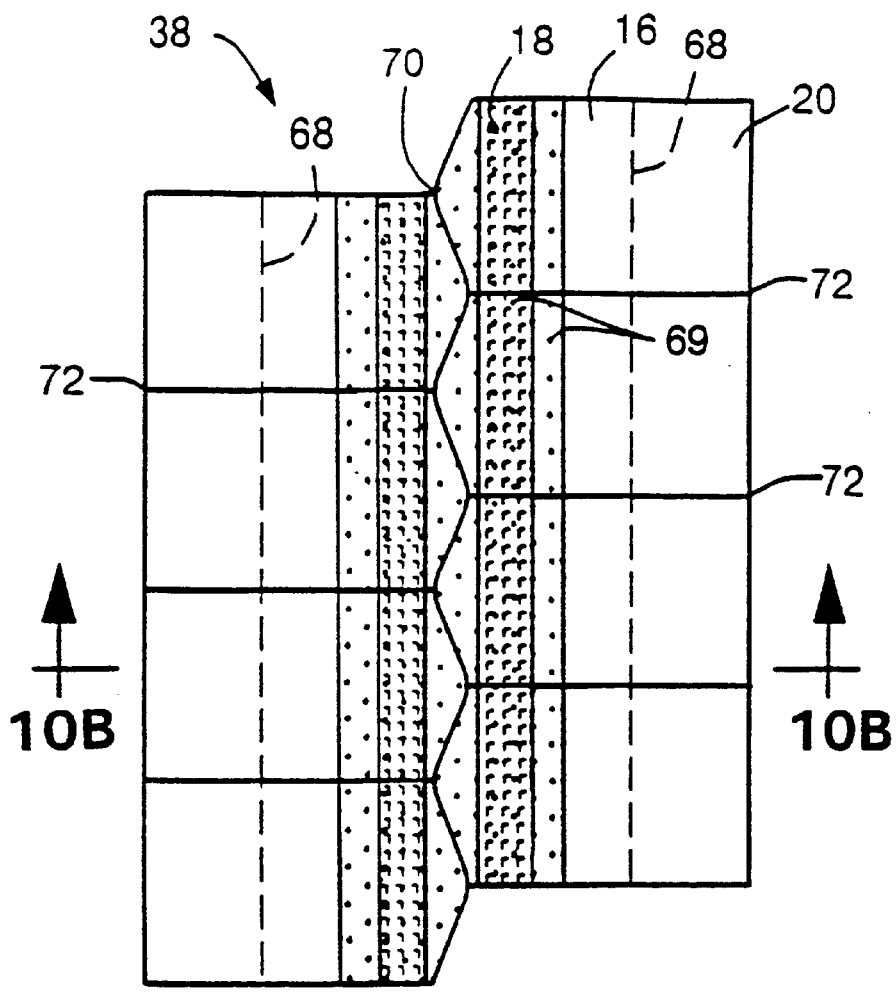
FIG. 9B is a plan view of fastening tapes manufactured by the process illustrated in FIG. 8B.
Figure 10B:
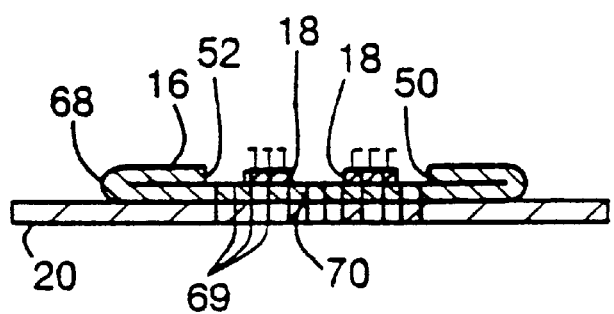
FIG. 10B is a cross-sectional view taken along line 10B—10B of FIG. 9B.

FIGS. 9A and 10A illustrate the fastening tapes formed by the process illustrated in FIG. 8A. FIGS. 9B and 10B illustrate the fastening tapes formed by the process illustrated in FIG. 8B. As can be seen from reference to FIGS.

9A and 10A, the fastening tapes produced by the method illustrated in FIG. 8A comprise a second substrate 20, a first substrate 16 folded to define fold line 68, and interlocking material 18. The adhesives used to form the fastening tapes 38 are not illustrated in FIGS. 9A, 9B, 10A and 10B. Fold line 68 is formed at folding area 48 of FIGS. 8A and 8B. Cutter 66 defines cut line 70, while cutter 36 defines cut lines 72. As will be appreciated more from the description of FIGS. 11 and 12, in use, the individual fastening tapes can be attached to a disposable absorbent garment by adhering the second substrate 20 to one surface of the garment and then unfolding the first substrate and adhering it to the opposite surface of the garment.

As can be seen from reference to FIGS. 9B and 10B, the fastening tape is identical to that described in connection with FIGS. 9A and 10A except for the presence of thermal (ultrasonic) bonds 69 and for the fact that the first substrate 16 is folded such that it does not overlay the interlocking material 18 but stops about 0.125 inch short of the interlocking material.

Applicants have found that, by having the first substrate 16 cover the interlocking material 18 as a result of folding at area 48, (as illustrated in FIG. 9A) processing of the fastening tape 38 may be improved. Specifically, the portion of the first substrate 16 covering the interlocking (hook) material 18 has been found to adhere to the interlocking material 18 during the process of conveying the fastening tape 38 to a location at which it is joined to the diaper. Further, covering the interlocking material 18 with the folded portion of the first substrate 16 has been found to keep adhesives used during the manufacturing process from contacting the hooks of the interlocking material.

Fastening tapes according to the present invention suitably have a width of from about 15 millimeters to about 100 millimeters, preferably of from about 25 millimeters to about 70 millimeters, and a length of from about 25 millimeters to about 150 millimeters, preferably of from about 50 millimeters to about 100 millimeters. Accordingly, the first and second substrates generally have a width of from about 15 millimeters to about 100 millimeters, preferably of from about 25 millimeters to about 70 millimeters, and a length of from about 50 millimeters to about 175 millimeters, preferably from about 60 millimeters to about 125 millimeters.

In those embodiments wherein the fastening tape comprises a first and a second substrate, the width and/or length of the first substrate may be equal to, greater, or less than, the width and/or length of the second substrate, and vice versa. In those embodiments wherein the first and second substrates have different lengths and/or widths, the length and width of the fastening tape may be defined by the combination of the first and second substrates. That is, for example, the length of the fastening tape may be greater than the length of either the first or second substrate alone.

The interlocking material may have a width (W") of from about 5 millimeters to about 50 millimeters, preferably of from about 10 millimeters to about 35 millimeters.

Figure 11:
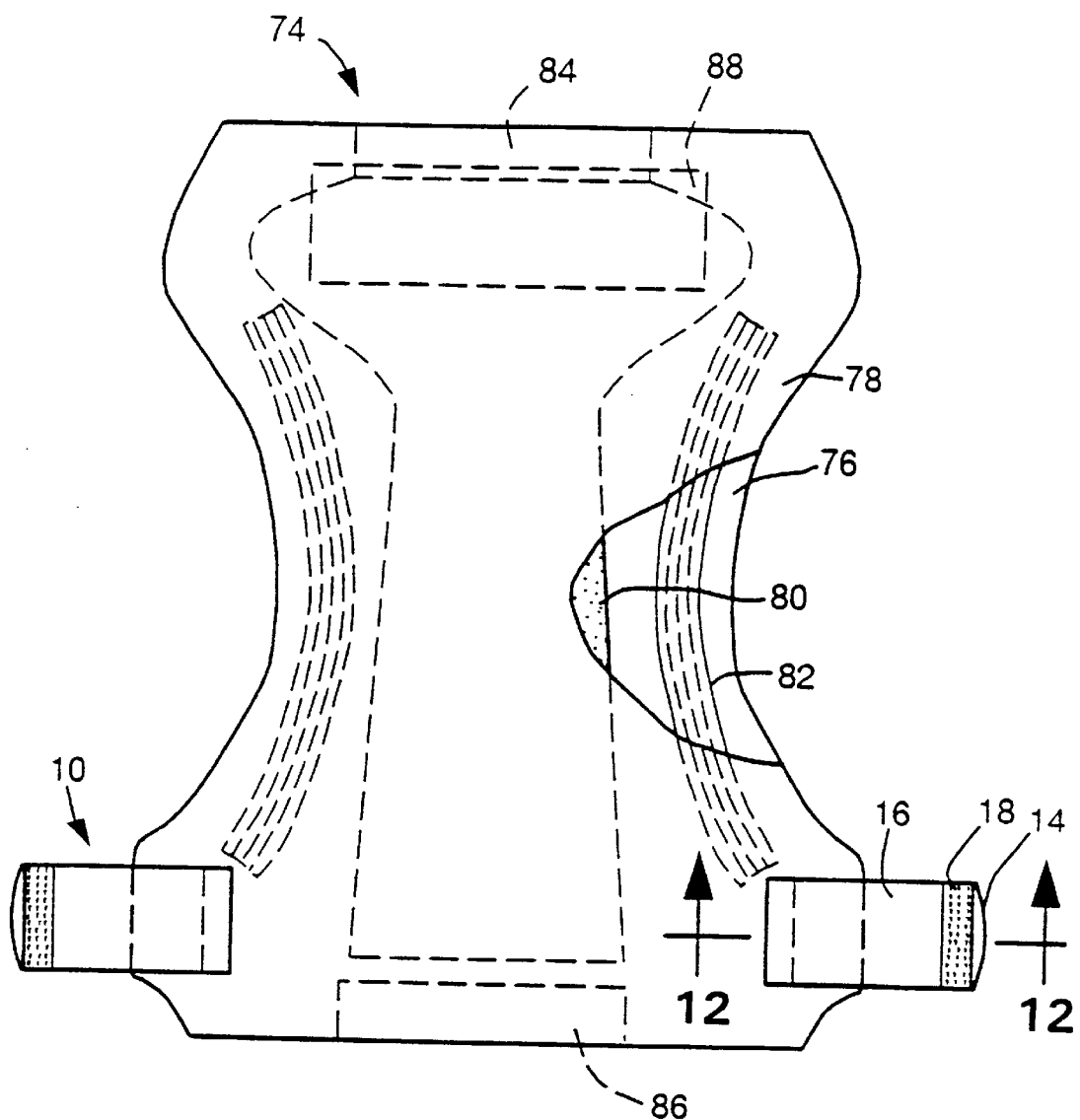
FIG. 11 illustrates a disposable infant diaper comprising fastening tapes according to the present invention.
Figure 12:
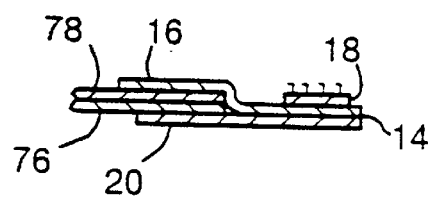
FIG. 12 is a cross-sectional view taken along line 12—12 of FIG. 11.

FIGS. 11 and 12 illustrate a fastening tape according to the present invention in use on a disposable diaper. Those skilled in the art will recognize that diaper 74 generally comprises an outer cover 76, an inner bodyside liner 78, and an absorbent core 80 located between the outer cover 76 and the liner 78. Leg elastics 82 are located generally at the longitudinal edges of diaper 74. The diaper further comprises a front waist elastic 84 and a rear waist elastic 86. The fastening tape of the present invention is generally attached at the rear of the diaper by sandwiching the outer cover 76 and inner bodyside liner 78 between the first substrate 16 and the second substrate 20 in an area where the first and second substrates are not attached to one another. This aspect of the present invention can best be seen by reference to FIG. 12. In the embodiment illustrated in FIG. 12, the second substrate 20 is not attached to the diaper 74 along as great a length as the first substrate 16. In the illustrated embodiment, interlocking material 18 comprises the hook material of the hook-and-loop fastener. The diaper further comprises a second interlocking material 88 attached to the outer cover 76 generally at the front of the diaper. In the illustrated embodiment, the second interlocking material 88 comprises the loop material of the hook-and-loop fastener. Those skilled in the art will recognize that the relative positions of the hook-and-loop materials could be reversed on diaper 74.

Specific examples of disposable absorbent garments on which the fastening tapes of the present invention may be utilized are disclosed in the following U.S. Patents and U.S. Patent applications: U.S. Pat. No. 4,798,603 issued Jan. 17, 1989, to Meyer et al.; U.S. Pat. No. 5,176,668 issued Jan. 5, 1993, to Bernardin; U.S. Pat. No. 5,176,672 issued Jan. 5, 1993, to Bruemmer et al.; U.S. Pat. No. 5,192,606 issued Mar. 9, 1993, to Proxmire et al., and U.S. patent application Ser. No. 07/757,760 filed Sep. 11, 1991, in the name of Hanson et al., abandoned in favor of Ser. No. 08/096,654, filed Jul. 22, 1993, now U.S. Pat. No. 5,509,915, issued Apr. 23, 1996.

EXAMPLES

Test Methods

Peel Strength

This test procedure determines the peak load, measured in grams force, required to remove the hook material from a fastening tape intended for use on a diaper.

Equipment

1. Tensile tester capable of obtaining a peak load and equipped with an appropriate load cell. A suitable tensile testing system is a Sintech Tensile Tester, commercially available from MTS Sintech, Research Triangle Park, North Carolina, under the trade designation Instron Model 4201 Tensile Tester with Sintech QAD (Quality Assurance Department) Software.

2. QAD software commercially obtained from MTS Sintech under the trade designation QAD Software.

3. 90 pound per square inch grips commercially available from Instron Corporation, Canton, Mass., under the trade designation "Grips Instron 2712 (90 psi), Instron 2712-003."

4. 0.5 inch grip faces, serrated, commercially available from Instron Corporation, Canton, Mass.

5. Test facility having a temperature of 23±1° C., and a relative humidity of 50±2 percent.

Test Procedure

Figure 13:
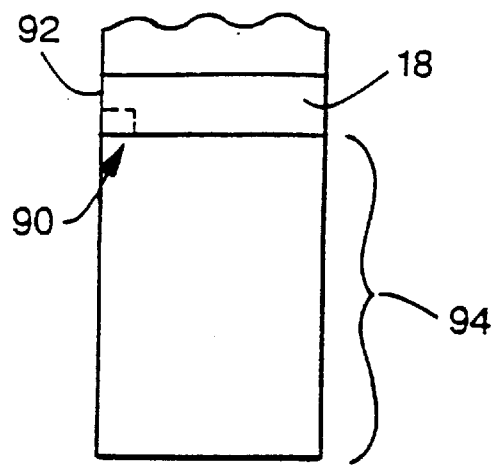
FIG. 13 illustrates a test sample for use in the peel and shear test described below in connection with the examples.

1. A sample to be tested, such as that illustrated in FIG. 13, is conditioned in the test facility for at least 4 hours prior to testing.

2. The load cell is calibrated and the QAD software loaded.

3. The grips are installed on the tensile tester with the serrated grip face being inserted into the upper jaw of the tensile tester and the jaw is closed.

4. The gauge length is set such that the distance from the bottom edge of the grip face to the top of the bottom grip is 1 inch.

5. One corner 90 of the hook material 18 present on the sample to be tested (FIG. 13) is gently peeled such that the hook material is separated from the first substrate for a distance of 8 millimeters from the side and edge of the hook material.

6. The test condition for the tensile tester are set as follows:

Crosshead speed: 250 millimeters/minute
Full-scale load: 10 kilograms
Threshold: 5 percent
Fail criterion: 95 percent
Gauge length: 1 inch
Sample width: 2 inches 7. The weight of the clamp is tared out.
8. The peeled edge of the hook material is inserted into the upper jaw such that the edge of the grip face is flush with the edge 92 of the hook material.
9. The longer portion 94 of the test sample is inserted into the lower jaw such that the hook material is positioned parallel to the edge of the lower jaw. The lower jaw is closed.
10. The crosshead is started in motion.
11. The peak load of failure is recorded. It is intended that the mode of failure is that the hook material delaminates from the first substrate. Results are rejected if the hook is torn along the edge of the grip face or if the peak load is below 2500 grams-force.

Shear Strength

This is pass/fail test that determines the length of time the hook material of a fastening tape can stay attached to a first substrate.

Equipment

1. A testing rack 100, such as that illustrated in FIG. 14, capable of fitting into a forced air oven which oven is commercially available from Blue M Electric Co., Blue Island, Ill. under the trade designation Stabil-Therm™.
2. Bulldog #4 clips. (3 inches wide) with emery cloth on the clamping portion. The clips, without emery cloth, are commercially available from Publix Office Supplies under the trade designation 3 inch Bulldog Clips. Emery cloth is attached through the use of adhesives.
3. Nalgene bottles (6 ounces) having a ¾ or ⅞ inch cup hook in the top. The bottles are commercially available from Nalgene Brand Products under the trade designation wide mouth Nalgene 6 ounce square bottles.
4. Lead shot to produce a total weight of 1000 grams including the nalgene bottle and clamp described as numbers 2 and 3 above.
5. A loop material commercially available from Guilford Mills, Greensborough, N.C., under the trade designation LP086. The loop material 102 is mounted on a solid surface cross bar of the testing rack illustrated in FIG. 14. The loop material must be in good condition to ensure consistent engagement with the hook material. Accordingly, the loop material should be replaced frequently, desirably after every test cycle.
6. An oven (such as the forced air oven described in the peel strength test) capable of holding the test rack illustrated in FIG. 14 which oven has a temperature of 37.8±1° C.
7. A testing facility having a temperature of 23±1° C. and a relative humidity of 50±2 percent.
8. A balance readable to 0.01 gram and having a minimum capacity of 1000 grams.

Test Procedure

Figure 14:
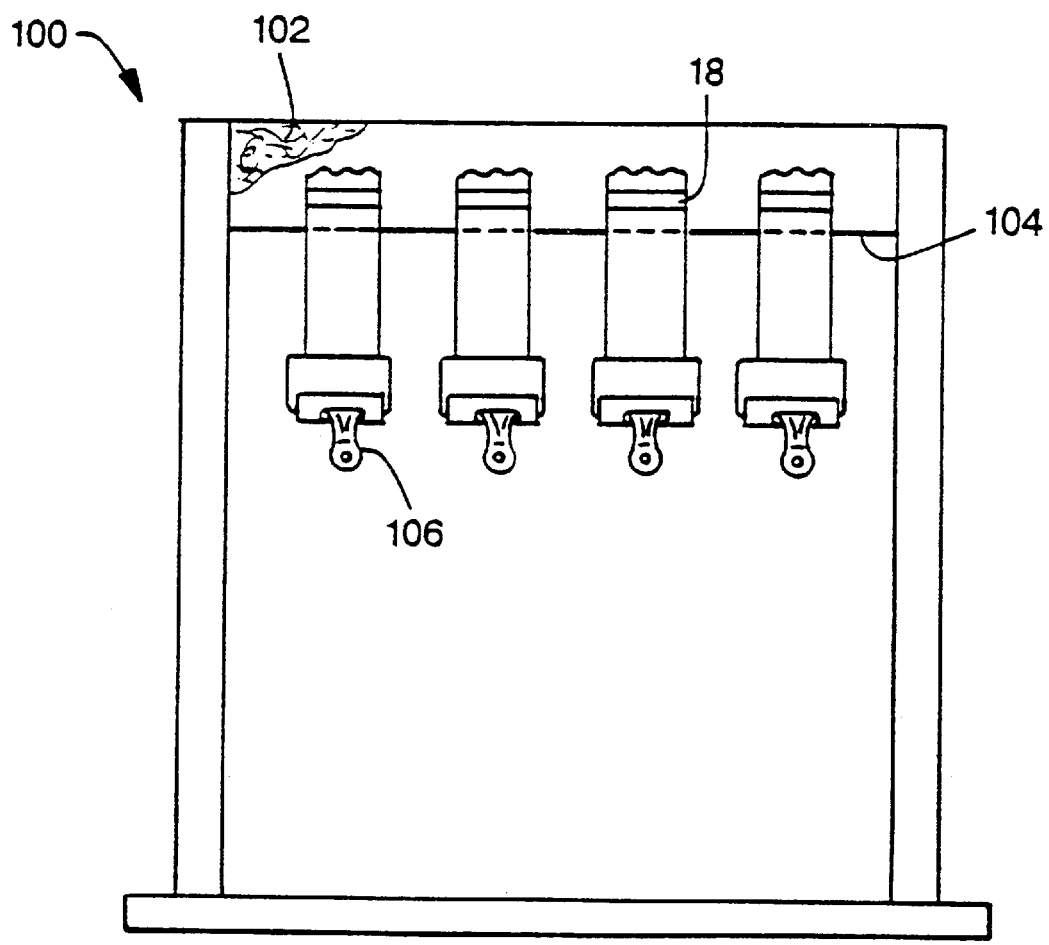
FIG. 14 illustrates a testing rack and test samples during the shear test described below in connection with the examples.

1. The sample to be tested is delivered to the testing facility and aged for at least 4 hours. The sample to be tested is attached to the testing rack such that the bottom edge of the hook material 18 present on the test samples is located ¾" from the bottom edge 104 of the loop material as illustrated in FIG. 14. A clamp 106 is attached to the bottom of the test sample as illustrated in FIG. 14. The test rack is placed in the oven.
2. A 1000 gram weight bottle (not illustrated) is attached to the clamp such that the bottles are hanging freely and such that there is at least ¾ of an inch between the bottom of the bottle and the bottom of the test rack or oven floor.
3. The samples are checked each hour noting which samples have failed. The test is run for a total of 20 hours. A failure is defined as the hook piece coming totally loose from the fastening tape. Results of the test are discarded if the hook and loop materials become totally or partially disengaged. The bottle, clamp, and ear laminate will be on the bottom of the testing rack or oven floor. The results of the test are recorded as a pass or a fail.

Example 1

A fastening tape test sample is prepared as follows. A first substrate comprising a 23.8 gram per square meter polypropylene spunbond web is provided. The first substrate has a width of 14.6 centimeters and a substantially continuous length. A hook material having a width of 1.27 centimeters (2.54 centimeter original width split to 1.27 centimeter) and a substantially continuous length is provided. The hook material is commercially available from Velcro U.S.A. under the trade designation CFM-22. Three beads having a diameter of about 1 millimeter of a hot melt adhesive commercially available from Findley Adhesives under the trade designation H2096 are applied to the non-hook surface of the hook material such that one bead is located in the center of the hook material and the other two beads are located about 4.5 millimeters from the center bead of adhesive. The hook material is applied to the first substrate and compressed at a pressure of 50 pounds per square inch to ensure adhesion.

A second substrate comprising a 57.8 gram per square meter spunbond/meltblown/spunbond (SMS) material is provided. The SMS fabric comprises two 21.25 gram per square meter polypropylene spunbond outer layers and on 15.3 gram per square meter polypropylene meltblown layer. The second substrate has a width of 15.24 and a substantially continuous length. The first substrate and second substrate are laminated together through the use of a hot melt adhesive commercially available from Findley Adhesives under the trade designation H2096. The hot melt adhesive is applied to the second substrate in a swirl pattern at an add-on rate of 0.0275 grams per square inch. The first and second substrates are compressed together under a load of 50 pounds per square inch to ensure adhesion.

The laminate of the hook material, first substrate, and second substrate is subjected to ultrasonic bonding under the following conditions. A rotary ultrasonic horn and a rotary patterned anvil such as those described in U.S. Pat. No. 5,110,403 and U.S. Pat. No. 5,096,532 are provided. The peak-to-peak amplitude of the horn is 0.001 inch (25.4 micrometers) and 40 pounds-force are applied between the horn and the anvil. The speed of travel through the rotary horn and anvil is about 67 feet per minute. Suitable speeds of travel for the laminate are from about 0 to about 500 feet per minute, alternatively, from about 50 to about 200 feet per minute. As the speed of travel of the laminate increases, the peak-to-peak amplitude of the horn is increased to obtain desirable bonds.

The ultrasonic bonding pattern consists of circular dots having a diameter of 0.064 centimeters spaced evenly over the planar surface of the hook material such that between about 2 and 3 percent of the surface area of the hook material is subjected to ultrasonic bonding.

Test samples are cut from the laminate of the hook material, first substrate, and second substrate. The test samples are 2 inches (5.08 centimeters) wide and 2–3 inches (5.08–7.6 centimeters) long. The hook material extends across the width of the test samples such that the hook material is located 0.25–0.5 inch (0.64–1.27 centimeters) from one transverse edge of the test sample and 1–2 inches (2.54–5.08 centimeters) from the opposite transverse edge of the test sample. That is, the test samples have generally the configuration illustrated in FIG. 13, with the understanding that the first and second substrates are coextensive.

The test samples are then subjected to the shear and peel testing described above.

Control samples are prepared as described above with the exception that Control A has only adhesive attaching the hook material to the first substrate and Control B has only ultrasonic bonding attaching the hook material to the first substrate (due to the nature of the ultrasonic bonding it also bonds the first and second substrates together). The control samples are then subjected to the peel and shear testing described above. The results of this testing are set forth in Table 1.

TABLE 1

| Sample | Peel[1] | Shear[2] |
| --- | --- | --- |
| 1 | 5058[3] | 0/20 |
| Control A[4] | 4637[5] | 10/10 |
| Control B[6] | 3105[7] | 0/20 |

[1]Peel adhesion in grams-force.
[2]Shear adhesion failures/number tested. Thus, 0/20 indicates 0 failures out of 20 test samples.
[3]Average of 10 samples, standard deviation = 917
[4]Adhesive only
[5]Average of 99 samples, standard deviation = 989
[6]Ultrasonic bonding only
[7]Average of 20 samples, standard deviation = 982

As can be seen from reference to Table 1, the presence of adhesive bonding alone (Control A) produces a fastening tape having generally acceptable peel adhesion but having unacceptable shear adhesion. The presence of ultrasonic bonds alone (Control B) produces a fastening tape having generally acceptable shear adhesion but unacceptable peel adhesion. The combination of the two types of bonding (Sample 1) produces a fastening tape having both acceptable shear and peel adhesion.

While the present invention has been described in terms of the specific embodiments set forth herein, those skilled in the art will recognize numerous variations and alterations thereof which are intended to be within the scope of the claims appended hereto.

What is claimed is:

1. A fastening tape for use on a disposable absorbent garment, said fastening tape having a width, a length, a first transverse edge and a second transverse edge, said fastening tape comprising:

a first substrate having a width;

an interlocking material attached to said first substrate and extending the entire width of said fastening tape.

2. The fastening tape according to claim 1 wherein said first substrate defines the width and length of said fastening tape.

3. The fastening tape according to claim 1 wherein said interlocking material is longitudinally spaced from both said first and said second transverse edges of said fastening tape by a distance of at least about 2 millimeters.

4. The fastening tape according to claim 1 further comprising a second substrate attached to said first substrate, said first and second substrates defining the width and length of said fastening tape.

5. The fastening tape according to claim 1 wherein said interlocking material is longitudinally spaced from both said first and said second transverse edges of said fastening tape by a distance of at least about 8 millimeters.

6. The fastening tape according to claim 4 wherein said second substrate is unattached to said first substrate in an area in which they overlap.

7. The fastening tape according to claim 1 wherein said interlocking material is attached to said first substrate such that a longitudinal edge of said interlocking material is not directly attached to said first substrate.

8. The fastening tape according to claim 1 wherein said interlocking material is attached to said first substrate along less than the entire width of the interlocking maternal to form an unattached edge.

9. The fastening tape according to claim 1 wherein said thermal bonds cover from about 1 to about 20 percent of a surface area of said interlocking material.

10. The fastening tape according to claim 9 wherein said thermal bonds cover from about 1 to about 10 percent of a surface area of sail interlocking material.

11. The fastening tape according to claim 10 wherein said thermal bonds cover from about 1 to about 5 percent of a surface area of said interlocking material.

* * * * *